(12) United States Patent
Linssen et al.

(10) Patent No.: US 8,017,078 B2
(45) Date of Patent: Sep. 13, 2011

(54) BLOOD CELL ANALYZER, BLOOD CELL ANALYZING METHOD, AND COMPUTER PROGRAM PRODUCT

(75) Inventors: Jo Linssen, Kerkrade (NL); Hans Kalkman, Uetersen (DE)

(73) Assignee: Sysmex Corporation, Kobe (JP)

( * ) Notice: Subject to any disclaimer, the term of this patent is extended or adjusted under 35 U.S.C. 154(b) by 224 days.

(21) Appl. No.: 12/002,973

(22) Filed: Dec. 19, 2007

(65) Prior Publication Data

US 2008/0199947 A1 Aug. 21, 2008

(30) Foreign Application Priority Data

Dec. 20, 2006 (JP) ................................. 2006-342228

(51) Int. Cl.
*G01N 27/00* (2006.01)
(52) U.S. Cl. ..................................... 422/82.01; 702/180
(58) Field of Classification Search ............... 422/82.01; 702/180
See application file for complete search history.

(56) References Cited

U.S. PATENT DOCUMENTS

| 4,735,504 | A | 4/1988 | Tycko |
| 6,525,807 | B1 * | 2/2003 | Morikawa et al. ............... 356/72 |
| 6,535,836 | B1 | 3/2003 | Grace |
| 7,267,798 | B2 * | 9/2007 | Chandler .................... 422/82.05 |
| 2005/0219527 | A1 | 10/2005 | Ikeuchi et al. |

FOREIGN PATENT DOCUMENTS

JP 11-326315 11/1999

* cited by examiner

*Primary Examiner* — Michael Marcheschi
*Assistant Examiner* — Jonathan Hurst
(74) *Attorney, Agent, or Firm* — Brinks Hofer Gilson & Lione

(57) ABSTRACT

A blood cell analyzer is provided with a first detection unit for electrically detecting blood cells in blood sample; a second detection unit for optically detecting blood cells in blood sample; a volume information obtainer for obtaining volume information of red blood cells based on the electrically detected blood cells; a scattered light intensity information obtainer for obtaining a scattered light intensity of red blood cells based on the optically detected blood cells; a first histogram preparer for preparing a first histogram of the volume information of each of red blood cells; a second histogram preparer for preparing a second histogram of the scattered light intensity information of each of red blood cells; a display unit; and a data processor for preparing a screen for displaying on the display unit, the screen including the first and second histograms.

7 Claims, 10 Drawing Sheets

US 8,017,078 B2

BLOOD CELL ANALYZER, BLOOD CELL ANALYZING METHOD, AND COMPUTER PROGRAM PRODUCT

CROSS REFERENCE TO RELATED APPLICATIONS

This application claims the benefit of priority from Japanese Patent Application 2006-342228, filed on Dec. 20, 2006, the entire disclosure of which is incorporated herein by reference.

FIELD OF THE INVENTION

The present invention relates to a blood cell analyzer capable of measuring blood cells in a measurement sample, and outputting information useful for the diagnosis and treatment of blood diseases and the like, to a blood cell analyzing method, and to a computer program product thereof.

BACKGROUND

Anemia is a blood condition in which there is a reduction in number of red blood cells, and the amount of hemoglobin contained in the red blood cells is also reduced. Anemia is generally screened on the basis of measurement results of items such as the red blood cell count (RBC), amount of hemoglobin (HGB), hematocrit value (HCT), mean cell volume (MCV), mean cell hemoglobin (MCH), mean cell hemoglobin concentration (MCHC) and the like obtained from a blood cell analyzer. However, it is difficult to distinguish the type of anemia by such a screening examination even though the degree of anemia can be determined. Since there are various causes of anemia, a physician can not be sure of the precise treatment to pursue because the type of anemia can not be identified.

Iron deficiency anemia and β thalassemia, for example, are caused by blood disease. Both diseases are caused by impeded production of red blood cells, and exhibit low values for MCV and MCH. It is difficult to distinguish between iron deficiency anemia and β thalassemia because low hemoglobin is a characteristic of small cells. Furthermore, it is difficult to differentiate between mild (minor) cases of β thalassemia and iron deficiency anemia.

The following facts are known based on this background and experiments were performed to classify types of anemia based on information obtained from blood cell analyzers.

(1) U.S. Pat. No. 4,735,504 discloses art which provides information concerning erythrocytic disease and anemic conditions through the determination of individual red cell volume (V) and hemoglobin concentration (HC) by flowing a sample liquid containing blood cells through a flow cell and detecting and analyzing two types of light signals which are emitted from the particles at different angles.

(2) Japanese Laid-Open Patent Publication No. 11-326315 discloses art which discriminates between juvenile blood, iron deficiency anemia, and β thalassemia foremost by utilizing a predetermined method on a plurality of data obtained from a blood analyzer.

(3) U.S. Pat. No. 6,535,836 discloses art which determines blood anomalies by setting a lower limit value and an upper limit value determined from the particle size distribution of normal blood on a particle size distribution curve for red blood cells.

(4) U.S. Pat. No. 6,535,836 discloses art which determines iron metabolism anomalies by combining three parameters obtained from several types of clinical examinations as a method for identifying anemia. The parameters used include the percentage of low hemoglobin red blood cells (HRC %) and the hemoglobin content in reticulocytes (CHr).

(5) US Laid-Open Patent Publication No. 2005-0219527 discloses art which discriminates types of anemia by calculating the reticulocyte hemoglobin content (RET-He) and hemoglobin content in mature red blood cells (RBC-He) from the forward scatter light intensity and the side fluorescent light intensity coming from individual blood cells obtained from a blood analyzer.

Since several examinations are normally necessary to diagnose anemia, it would be extremely beneficial from the perspective of clinical examinations if suitable treatment could be provided at an early stage and at low cost using only a blood cell analyzer without performing a special examination to provide useful identification information.

SUMMARY

The scope of the present invention is defined solely by the appended claims, and is not affected to any degree by the statements within this summary. A blood cell analyzer embodying features of the present invention includes: a first detection unit for electrically detecting blood cells in blood sample; a second detection unit for optically detecting blood cells in blood sample; a volume information obtainer for obtaining volume information of red blood cells based on the electrically detected blood cells by the first detection unit; a scattered light intensity information obtainer for obtaining a scattered light intensity of red blood cells based on the optically detected blood cells by the second detection unit; a first histogram preparer for preparing a first histogram of the volume information of each of red blood cells obtained by the volume information obtainer; a second histogram preparer for preparing a second histogram of the scattered light intensity information of each of red blood cells obtained by the scattered light intensity information obtainer; a display unit; and a data processor for preparing a screen for displaying on the display unit, the screen including the first and second histograms prepared by the first and second histogram preparer.

A blood cell analyzing method embodying features of the present invention includes steps of: electrically detecting blood cells in blood sample; optically detecting blood cells in blood sample; obtaining volume information of red blood cells based on the electrically detected blood cells; obtaining scattered light intensity information of red blood cells based on the detected optically blood cells; preparing a first histogram using as parameters the volume information of each of red blood cells; preparing a second histogram using as parameters the scattered light intensity information of each of red blood cells; and displaying a screen including the first and second histograms.

A computer program product for enabling a computer to execute a method of analyzing blood cells in a biological sample, the computer program product embodying features of the present invention includes: a computer readable medium; and software instructions, on the computer readable medium, for enabling the computer to perform predetermined operations comprising: electrically detecting blood cells in blood sample; optically detecting blood cells in blood sample; obtaining volume information of red blood cells based on the electrically detected blood cells; obtaining scattered light intensity information of red blood cells based on the detected optically blood cells; preparing a first histogram using as parameters the volume information of each of red blood cells; preparing a second histogram using as parameters the scattered light intensity information of each of red blood cells; and displaying a screen including the first and second histograms.

DETAILED DESCRIPTION OF THE PREFERRED EMBODIMENTS

The embodiment of the blood cell analyzer of the present invention is described hereinafter with reference to the drawings.

Figure 1:
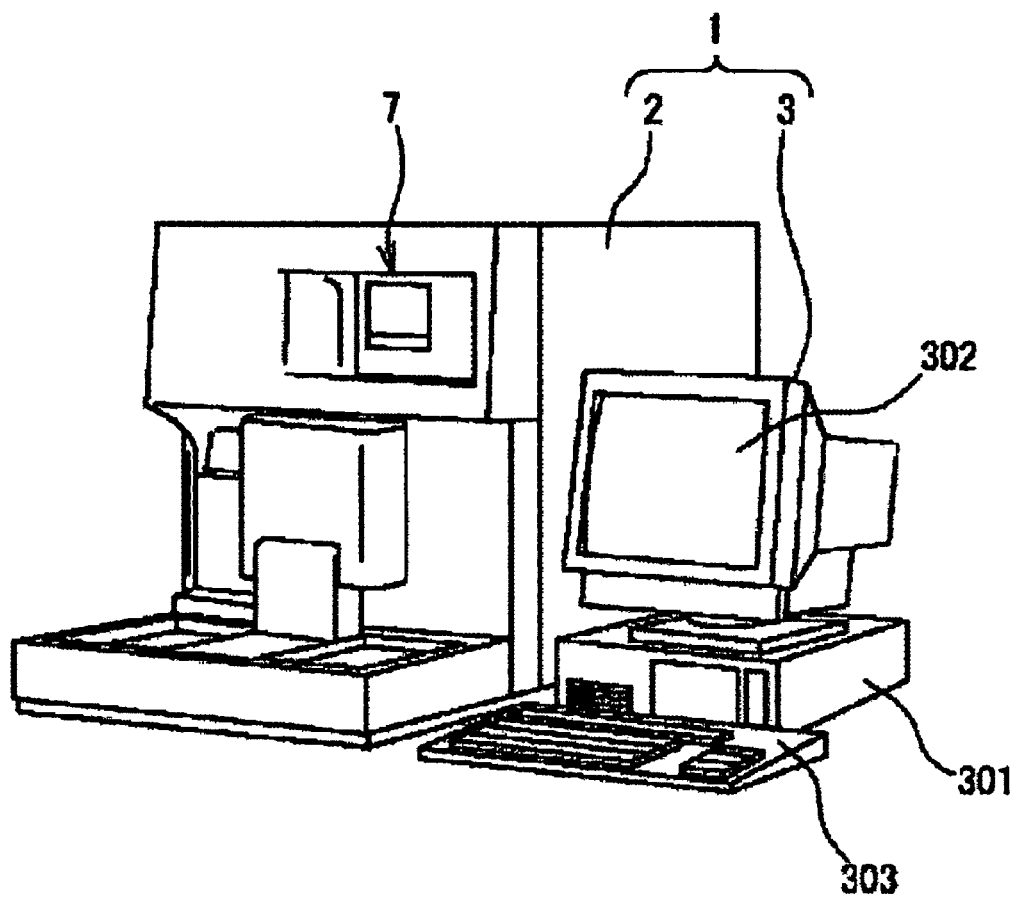
FIG. 1 is an external view of an embodiment of the blood cell analyzer of the present invention.

FIG. 1 is an external view of an example of a blood cell analyzer. This apparatus is configured as a multifunction automatic blood cell analyzer, which has functions to measure a blood sample contained in a sample container (blood collection tube), and output the measurement results to a display or the like. The analyzer classifies and counts mature blood cells such as white blood cells, red blood cells, platelets and the like, as well as immature blood cells.

The blood cell analyzer 1 is configured by a measuring device 2 which is provided with a fluid processing unit for diluting blood in a sample with dilution fluid and reacting the blood with reagent, a detection unit for detecting particle signals of the prepared measurement sample, and a signal processing unit for processing the detected particle signals, the blood cell analyzer 1 is also provided with a data processing device 3 which processes and stores the data obtained by the measuring device 2 and outputs the measurement results. Although the blood cell analyzer 1 of the present embodiment is configured by the measuring device 2 and data processing device 3 which are separate devices, both may be integrated as a single apparatus. The measuring device 2 is provided with a display and operating unit 7. The data processing device 3 is provided with a data processing unit 301, display unit 302, and input unit 303.

Each part of the blood cell analyzer 1 is described in detail below.

Figure 2:
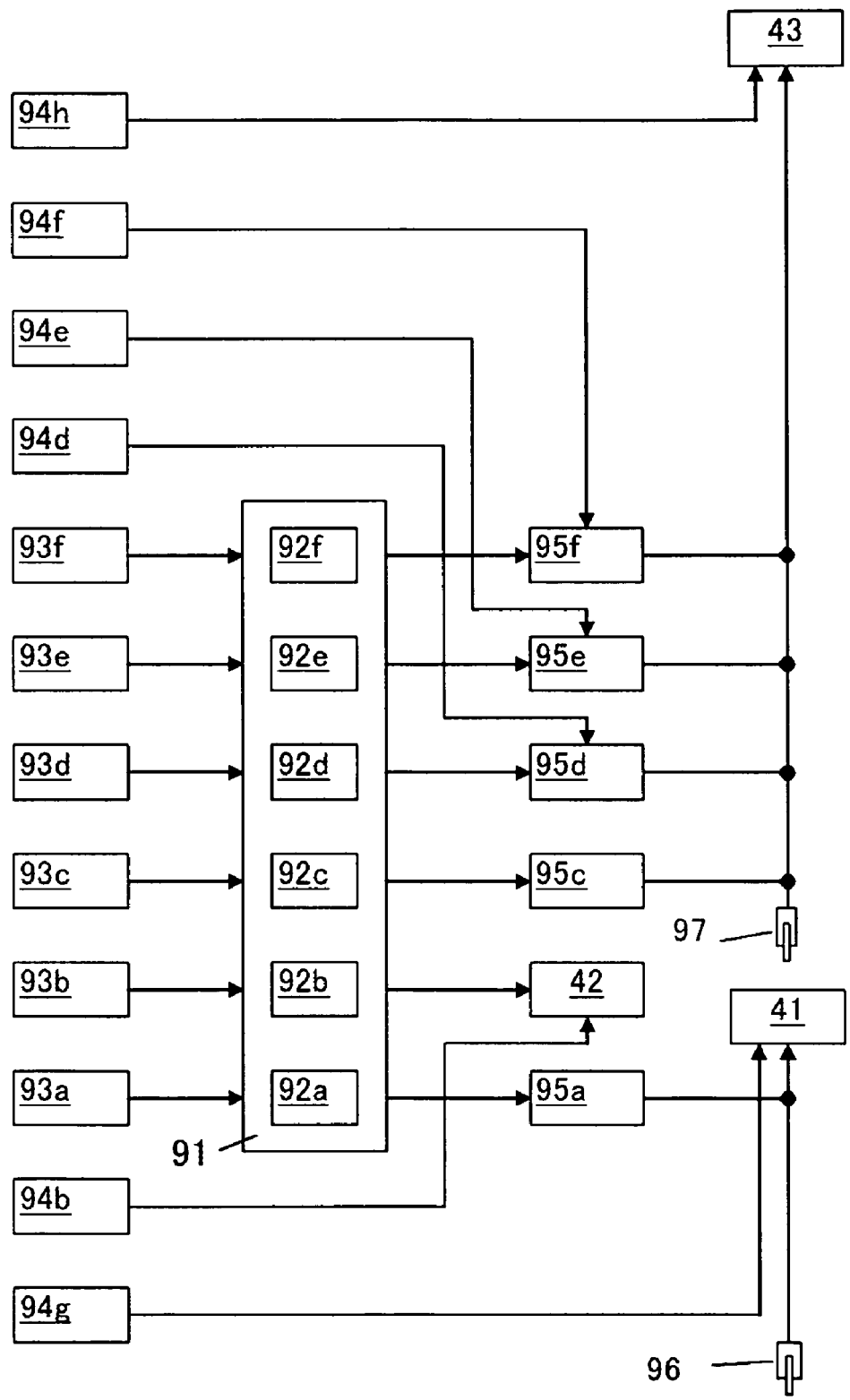
FIG. 2 is a block diagram of the fluid processing unit.
Figure 5:
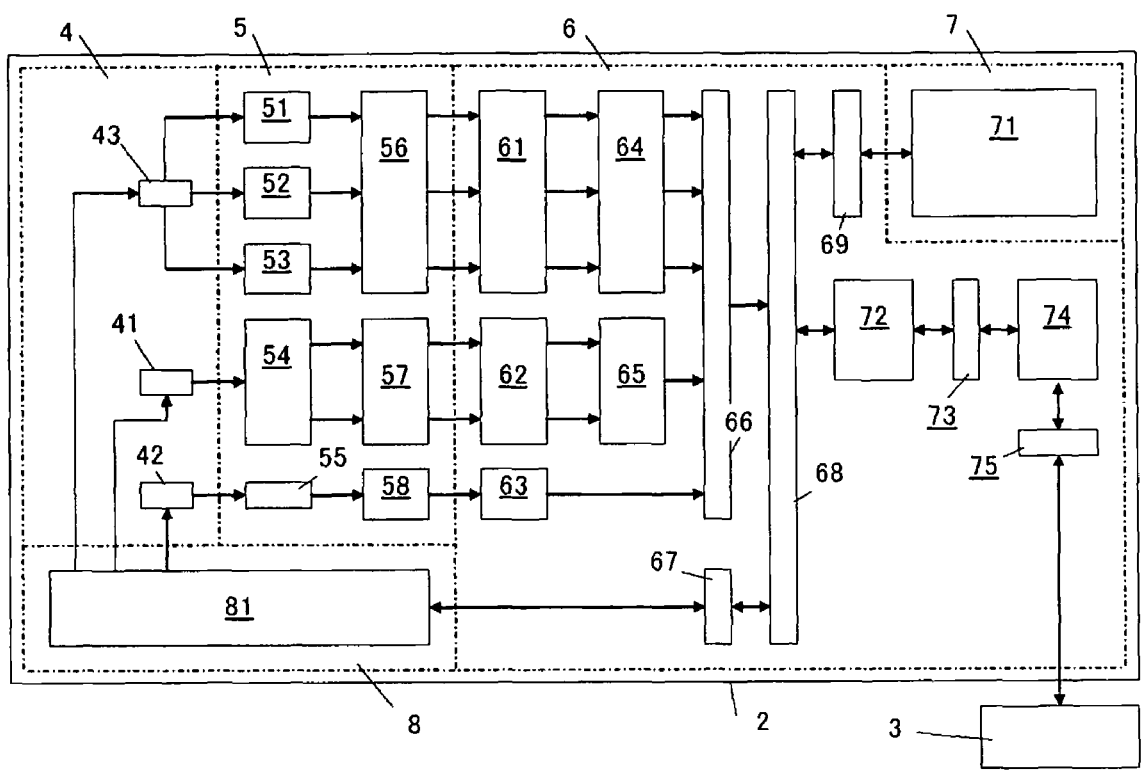
FIG. 5 is a block diagram of a measuring device.

FIG. 2 is a block diagram of a fluid processing unit 81 (refer to FIG. 5).

The blood, that is, the sample, within the test tube is aspirated by set dosage pump (not shown in the drawing) and introduced to a sampling valve 91. Measurement samples are prepared by collecting fixed quantities of sample in the sampling valve 91, and mixing the collected fixed quantity samples 92a through 92f with reagents which are supplied fixed quantities of dilution fluid and reagents by dosage pumps 93a through 93f, in reaction chambers 95a through 95f.

The fixed quantity sample 92f collected in the sampling valve 91 is supplied to the reaction chamber 95f together with a fixed quantity of dilution fluid supplied by a dosage pump 93f. A fixed quantity of stain is also supplied to the reaction chamber 95f by a dosage pump 94f. Measurement samples are prepared for four types of white blood cells (4DIFF) by combining the sample 92f, dilution fluid, and stain in the reaction chamber 95f.

The fixed quantity sample 92e collected in the sampling valve 91 is supplied to the reaction chamber 95e together with a fixed quantity of dilute hemolytic agent supplied by the dosage pump 93e. A fixed quantity of stain is also supplied to the reaction chamber 95e by a dosage pump 94e. A measurement sample for nucleated red blood cells (NRBC) is prepared by combining the sample 92e, dilute hemolytic agent, and stain in the reaction chamber 95e.

The fixed quantity sample 92d collected in the sampling valve 91 is supplied to the reaction chamber 95d together with a fixed quantity of dilution fluid supplied by the dosage pump 93d. A fixed quantity of stain is also supplied to the reaction chamber 95d by a dosage pump 94d. A measurement sample for reticulocytes (RET) is prepared by combining the sample 92d, dilution fluid, and stain in the reaction chamber 95d. The reagent kit "RET search II" which is manufactured by Sysmex Corporation is suitable for use as the dilution fluid and stain. The stain in this reagent kit contains ethylene glycol and polymethene dyestuff, and is capable of staining erythrocytes, reticulocytes, and platelets.

The fixed quantity sample 92c collected in the sampling valve 91 is supplied to reaction chamber 95c together with a fixed quantity of dilute hemolytic agent supplied by the dosage pump 93c. A measurement sample for white blood cells and basophils (WBC/BASO) is prepared by combining the sample 92c and dilute hemolytic agent in the reaction chamber 95c.

The fixed quantity sample 92a collected in the sampling valve 91 is supplied to the reaction chamber 95a together with a fixed quantity of dilution fluid supplied by the dosage pump 93a. A measurement sample for red blood cells and platelets (RBC/PLT) (hereinafter referred to as "RBC sample") is prepared by combining the sample 92a and dilution fluid in the reaction chamber 95a.

The hemoglobin (HGB) measurement sample, which is a mixture of the fixed quantity sample 92b collected by the sampling valve 91 and the fixed quantity dilute hemolytic agent supplied by the dosage pump 92b, is supplied to a hemoglobin detection unit 42. The hemoglobin detection unit 42 measures the absorption light of the hemoglobin (HGB) measurement sample.

The NRBC sample in the reaction chamber 95e, the WBC/BASO sample in the reaction chamber 95c, the 4DIFF sample in the reaction chamber 95f, and the RET sample in the reaction chamber 95d are sequentially introduced to an optical type detection unit 43 by a dosage syringe 97. The block 94h is a means for supplying sheath liquid to the detection unit 43.

The RBC sample in the reaction chamber 95a, however, is introduced to an electrical resistance type detection unit 41 by a dosage syringe 96. The block 94g is a means for supplying sheath liquid to the detection unit 41.

Thus, the detection unit 4 is provided with an electrical resistance type detection unit 41 for measuring red blood cells, s hemoglobin detection unit 42 for detection the amount of hemoglobin in blood cells, and an optical type detection unit 43 for detecting white blood cells and reticulocytes.

The detection units 41 and 43 are described in detail below.

Figure 3:
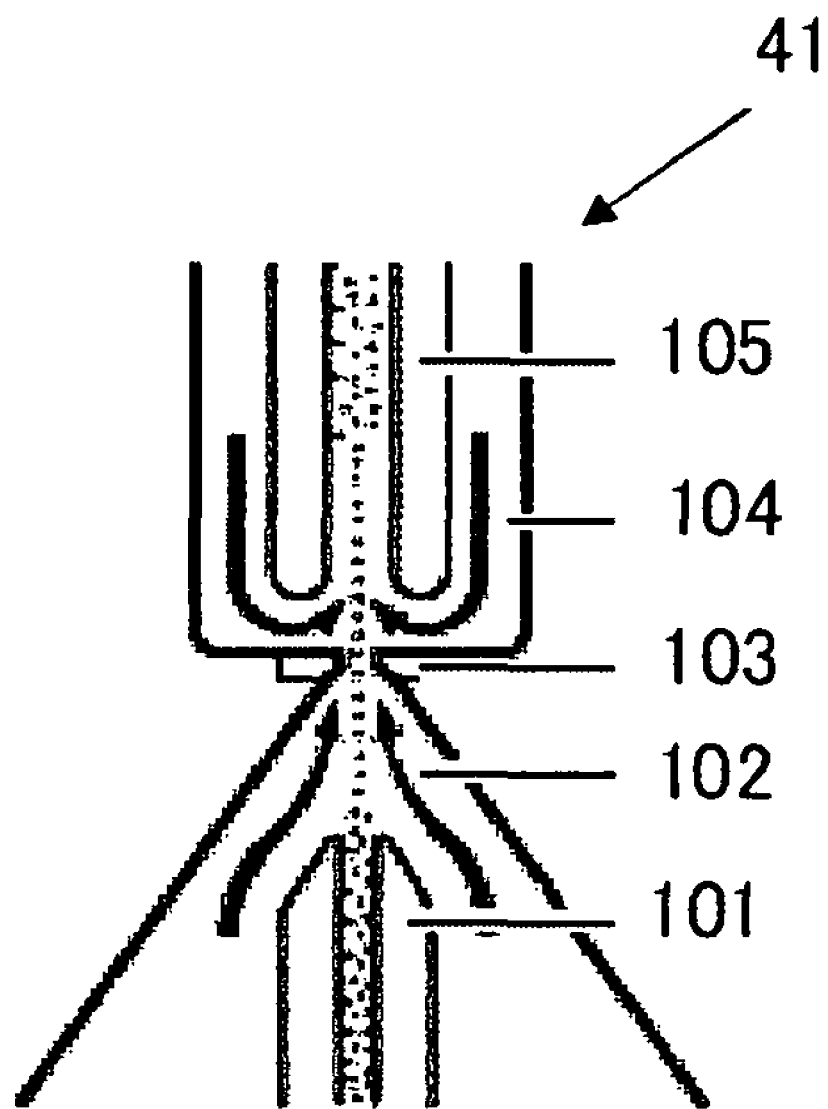
FIG. 3 is a schematic view of an example of an electrical resistance type detection unit.

FIG. 3 shows an example of the electrical resistance type detection unit 41 using a sheath flow. The RBC sample containing red blood cells is extracted from a nozzle 101 at a constant speed by a dosage syringe 96 and encapsulated by a surrounding front sheath liquid 102 before passing through an orifice 103. After passing through the orifice, the measurement sample is collected together with a back sheath 104 in a recovery tube 105. Electrodes (not shown in the drawing) are disposed so as to have the orifice 103 interposed therebetween, and the peak values of particle signals, which are proportional to the volume of the particle, are detected for each particle flowing through the orifice 103.

Figure 4:
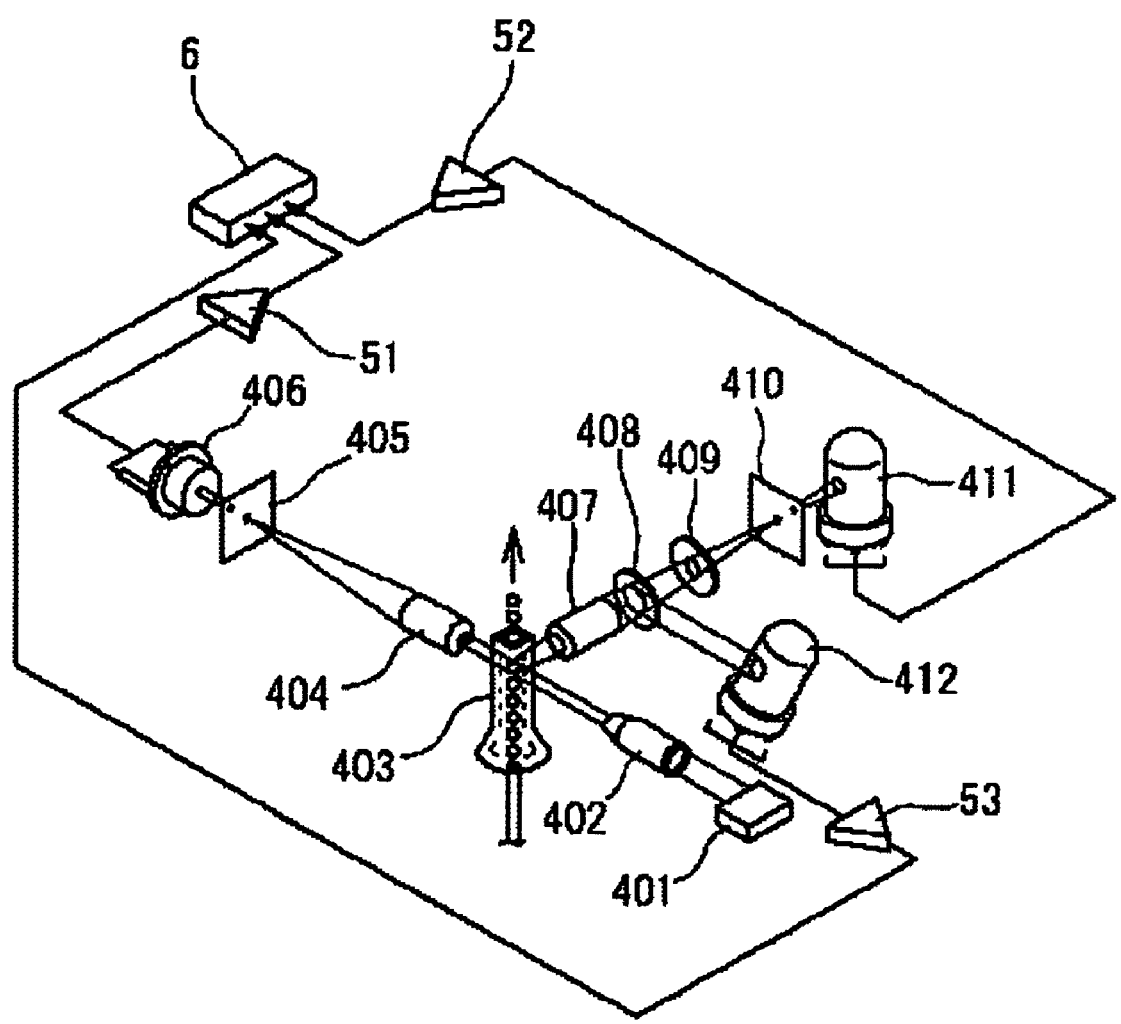
FIG. 4 is a perspective view of an example of an optical type detection unit.

FIG. 4 shows the detection unit 43 for optically measuring particles. The measurement samples prepared in the reaction chambers 95e, 95c, 95f, and 95d are extracted from nozzles at constant speed by a dosage syringe 47 and encapsulated by a surrounding sheath liquid before flowing through the orifice of the sheath flow cell 403. A laser beam emitted from a laser diode 401 irradiates the orifice area of the sheath flow cell 403 through a collimator lens 402. The forward scattered light from blood cells passing through the region of the orifice irradiated by the laser beam enter a photodiode 406 through a collective lens 404 which is provided with a beam stopper, and a pin hole plate 405. Among the lateral light from the blood cells passing through the region of the orifice irradiated by the leaser beam, the side scattered light enters the a photomuliplier tube (hereinafter referred to as "photomultiplier") 412 through a collective lens 407 and a dichroic mirror 408, and the side fluorescent light enters an optical filter 409 via the dichroic mirror 408, then enters a photomultiplier 411 through a pinhole plate 410.

The forward scattered light signal from the photodiode 406 is subjected to various types of signal processing by a detection circuit 51, and thereafter send to a digital signal processing unit 6. The side scattered light signal from the photomultiplier 412 is subjected to various types of signal processing by a detection circuit 53, and thereafter sent to the digital signal processing unit 6. The side fluorescent light signal from the photomultiplier 411 is subjected to various types of signal processing by a detection circuit 52, and thereafter sent to the digital signal processing unit 6.

The signal processing and data processing are described in detail below.

FIG. 5 shows an example of a block diagram of the measuring device 2 of the analyzer.

The particle signals detected by the detection unit 4 are subjected to signal processing by a signal processing unit 5 which performs analog signal processing, and subjected to data processing and analysis by a digital signal processing unit 6 which performs digital signal processing, then the resulting signals are sent to a data processing device 3 which displays and stores the results. A mechanism and fluid unit 8 is provided with a fluid processing unit 81. The operation and display unit 7, which is provided in the measuring device 2, is provided with a touch panel type liquid crystal panel 71.

The forward scattered light signals, side scattered light signals, and side fluorescent light signals from the optical type detection unit 43 are detected and amplified by the respective detection circuits 51, 53, and 52. The signals from the electrical resistance type detection unit 41 are input to a detection circuit 54 and subjected to red blood cell signal processing and platelet signal processing, and respectively output. The signals from the hemoglobin detection unit 42 are detected and amplified by a detection circuit 55.

The signals from the detection circuits 51 through 54 are respectively subjected to waveform processing in waveform processing circuits 56 and 57 to eliminate noise and facilitate signal processing. The signals from the detection circuit 55 pass through a conversion circuit 58, and hemoglobin concentration data are determined by a counting circuit 63. After waveform processing, each particle signal is sequentially subjected to A/D conversion by A/D conversion circuits 61 and 62, and the A/D converted data are input to the distribution data generating units 64 and 65 and stored therein, and the final particle distribution data are generated.

When the distribution data are generated in the distribution generating units 64 and 65, a control processor 72 obtains the distribution data through an interface 66 and a bus 68, and the data are then sent to an analysis processor 74 through an interface 73. The analysis processor 74 analyzes clustering and the like in the distribution data. The analysis results are sent to an external data processing device 3 through an interface 75, and the data processing device 3 executes processes for screen display and storage of the data.

Details of the blood cell analysis are described below. The methods for performing particle analysis of the target red blood cells and providing information useful for the diagnosis and treatment of anemia are described below. Primary distribution data (histogram data) generated using as parameters the volume information obtained by measuring the RBC sample in the sheath flow electrical resistance type detection unit, and secondary distribution data (scattergram data) generating using as parameters the forward scattered light intensity and side fluorescent light intensity obtained by measuring the RET sample in the optical type detection unit are used. New information is obtained by analyzing the distribution data in the analysis processor.

Figure 6:
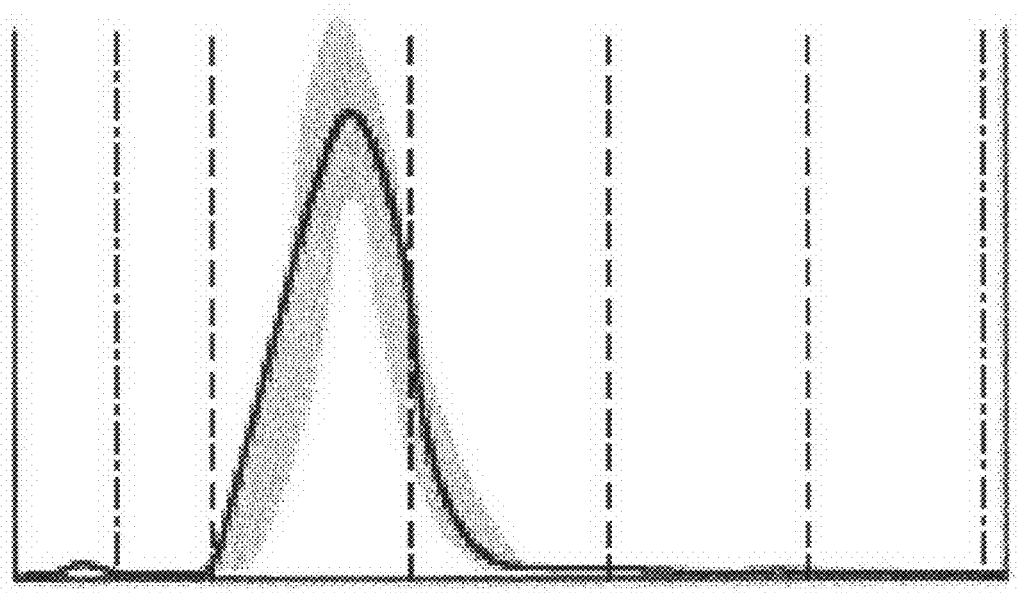
FIG. 6 shows an example of a distribution map of red blood cells detected by an electrical resistance type detection unit.
Figure 7:
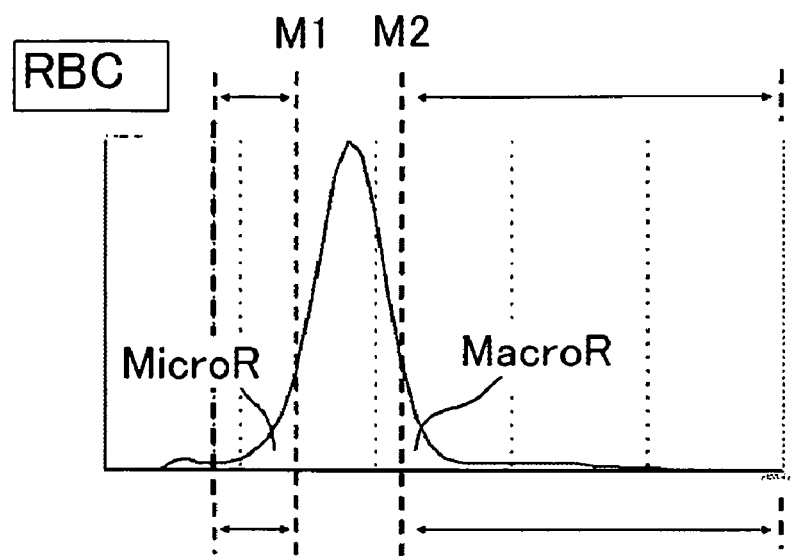
FIG. 7 shows thresholds displayed in the distribution map of FIG. 6.
Figure 10:
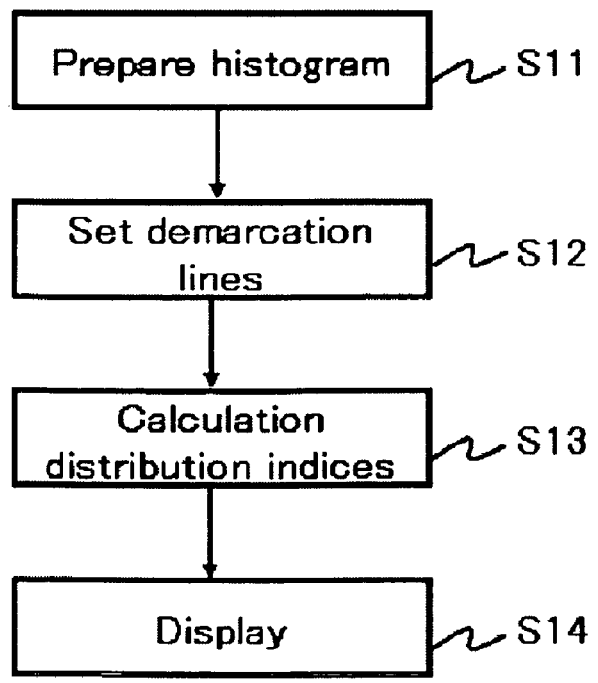
FIG. 10 shows an example of the flow of the analysis processing of data detected by the electrical resistance type detection unit.

FIG. 6 is a red blood cell histogram (RBC histogram) measured from the RBC sample, and FIG. 7 is a histogram displaying demarcation lines M1 and M2 in the histogram of FIG. 6. The horizontal axis of the histograms of FIGS. 6 and 7 (RBC histogram) is volume information (fL), and the vertical axis is the relative number (%). FIG. 10 is a flow chart of the analysis process.

The analysis processor 74 generates an RBC histogram shown in FIG. 6 when the distribution data obtained from the RBC sample is received from the distribution data generating unit 65 (step S11). The analysis processor 74 reads and displays the demarcation line (threshold value) M1 set for the small region and the demarcation line (threshold value) M2 set for the large region of the RBC histogram shown in FIG. 7 from memory (step S12). The demarcation line M1 is a value equivalent to 70 fL, and the demarcation line M2 is a value equivalent to 110 fL. Next, the analysis processor 74 calculates the percentage (MicroR) of red blood cells in the region below the demarcation line M1 relative to the total number of red blood cells in the RBC histogram, and calculates the percentage (MacroR) of red blood cells in the region above the demarcation line M2 relative to the total number of red blood cells (step S13). The analysis processor 74 then displays a display screen that includes the RBC histogram which uses the volume of red blood cells as a parameter, and the MicroR and MacroR on the display unit of the data processing unit (step S14).

Figure 8:
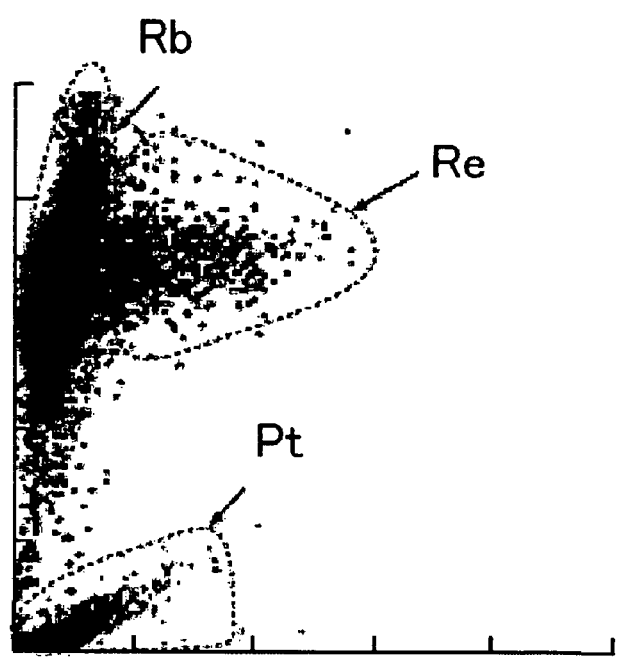
FIG. 8 shows an example of a distribution map of red blood cells detected by an optical type detection unit.
Figure 9:
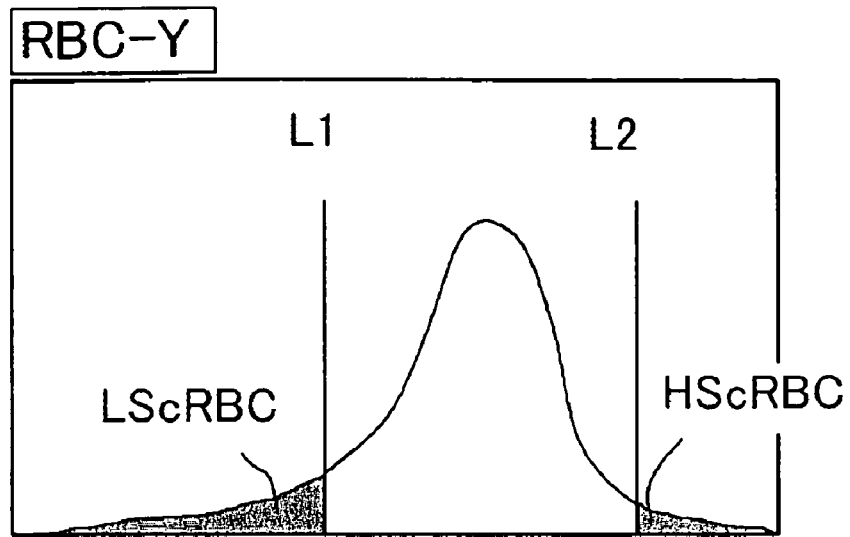
FIG. 9 shows a distribution map of red blood cells detected by an optical type detection unit.
Figure 11:
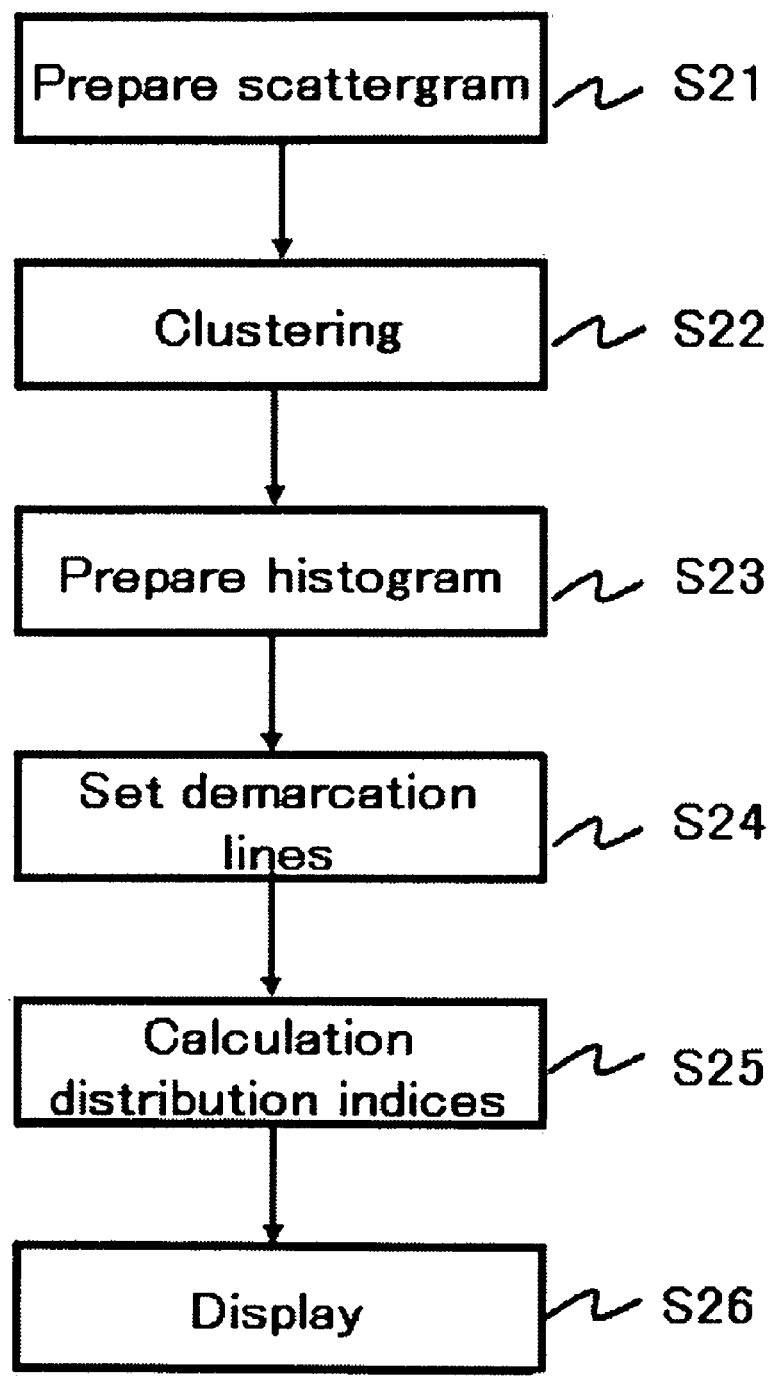
FIG. 11 shows an example of the flow analysis processing of data detected by the optical type detection unit.

FIG. 8 shows a scattergram obtained by measuring the RET sample (the vertical axis denotes forward scattered light intensity, and the horizontal axis denotes side fluorescent light intensity), and FIG. 9 shows a histogram obtained from the mature red blood cells Rb in the scattergram of FIG. 8 (the vertical axis denotes relative number, and the horizontal axis denotes forward scattered light intensity). FIG. 11 is a flow chart of the analysis process. In the scattergram of FIG. 8, Rb refers to mature the red blood cell distribution, Re refers to the reticulocyte distribution, and Pt refers to platelet distribution.

The analysis processor 74 generates the scattergram shown in FIG. 8 when distribution data obtained from the RET sample are received from the distribution generating unit 64 (step S21). The analysis processor 74 executes clustering analysis of the distribution data received from the distribution data generating unit 64 based on the scattered light intensity and fluorescent light intensity, and identifies the particles related to mature red blood cells Rb (step S22). The analysis processor 74 then generates a histogram using as parameters the forward scattered light of each particle identified as a mature red blood cell Rb (referred to as "RBC-Y histogram below") (step S23).

Next, the analysis processor 74 reads from memory and displays the demarcation line (threshold value) L1 set for the small region, and the demarcation line (threshold value) L2 set for the large region of the RBC-Y histogram shown in FIG. 9. The scattered light intensity of the red blood cells is a parameter which reflects the amount of hemoglobin contained in the red blood cells, the demarcation line L1 is a scattered light intensity which is equivalent to 27 pg of hemoglobin, and the demarcation line L2 is a scattered light intensity which is equivalent to 33 pg of hemoglobin. The analysis processor 74 calculates the percentage of red blood cells (LScRBC) in the region below the demarcation line L1 relative to the total number of red blood cells, and calculates the percentage of red blood cells (HScRBC) in the region above the demarcation line L2 in the RBC-Y histogram (step S25). The analysis processor 74 displays a display screen which includes the RBC-Y histogram generated using the forward scattered light intensity of red blood cells as a parameter, the LScRBC, and the HScRBC on the display unit of the data processing unit 2. Furthermore, the analysis processor 74 displays the RBC histogram side by side with the RBC-Y histogram on the display screen.

Figure 12:
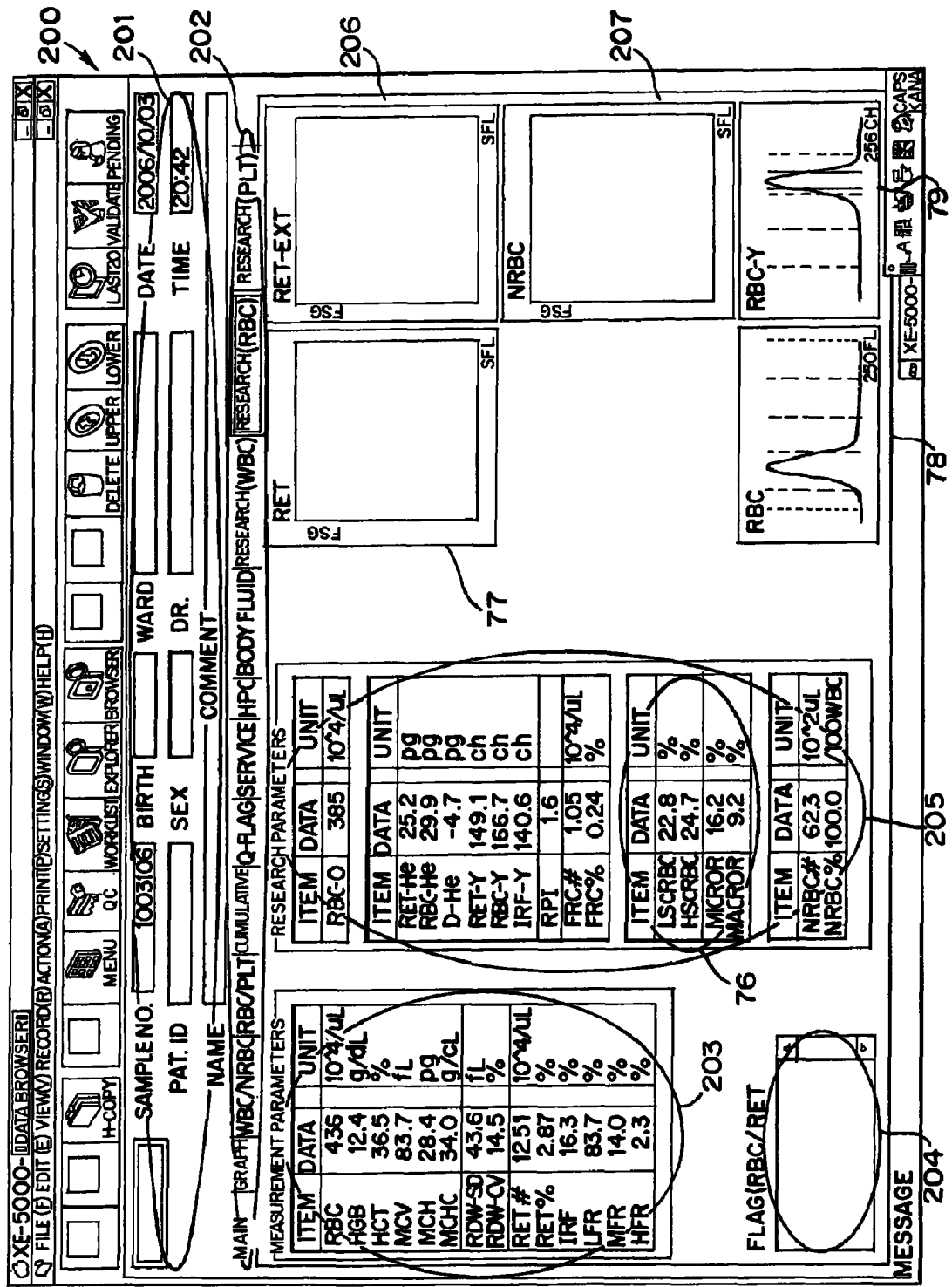
FIG. 12 shows a display screen displaying the analysis results.

FIG. 12 shows an example of a display screen 200.

An attribute display region 201 for displaying sample or patient attributes is provided at the top of the screen 200, and specifically, the sample number, patient name, sex, date of birth, ward, attending physician, date of measurement, time of measurement, comment and the like are displayed therein. A measurement result display region for displaying the results of a measurement is provided at the bottom of the attribute display region 201. Reference number 202 refers to tabs for switching the display content of the measurement result display region; there are a plurality of tabs which correspond to various items such as main menu, graph screen and the like. FIG. 12 shows the condition when the research (RBC related) tab is selected. A text display region for displaying numerical values and flags is provided in the left half of the measurement result display region, and a distribution map display region for displaying distribution maps is provided on the right half. Provided in the measurement result display region are a display region 203 for displaying the results of measurement items such as RBC, HGB, HCT, HFR and the like, a display region 204 for displaying flagging results related to RBC or RET, and a display region 205 for displaying research items such as RBC-O, RET-He, RBC-He, NRBC % and the like. A display region 76 is also provided for displaying the values of the four items of LScRBC, HScRBC, MicroR, and MacroR among the research items in the display region 205.

In this example, five distribution maps are displayed in the distribution map display region. The five distribution maps include an RET sample scattergram 77 in which the vertical axis denotes forward scattered light intensity and the horizontal axis denotes the side fluorescent light intensity, a scattergram 206 in which the scale of the horizontal axis of the scattergram 77 is changed in the display, an NRB sample scattergram 207 in which the vertical axis denotes the forward scattered light intensity and the horizontal axis denotes the side fluorescent light intensity, an RBC histogram 78, and an RBC-Y histogram 79. The RBC histogram, 78 and the RBC-Y histogram 79 are displayed side by side. Thus, Differences in the distributions of the histograms can be readily understood since the RBC histogram 78 and the RBC-Y histogram 79 are displayed side by side.

Furthermore, the demarcation lines M1 and M2 may be displayed in the RBC histogram 78, and the demarcation lines L1 and L2 may be respectively displayed in the RBC-Y histogram 79. Thus, differences in the distribution patterns can be readily understood by displaying the demarcation lines in the distribution maps. In the present embodiment, the demarcation lines L1 and L2 are displayed in the RBC-Y histogram.

The scattered light intensity which is used as a parameter for the RBC-Y histogram is information that reflects the size of the red blood cell, and also reflects the hemoglobin concentration in the red blood cell since it is measured optically. However, the RBC histogram uses the red blood cell volume as a parameter. β thalassemia characteristically has a low value for MicroR and a high value for LScRBC. Therefore, a physician can readily understand that a patient has β thalassemia by displaying the RBC histogram and RBC-Y histogram side by side.

Furthermore, iron deficiency anemia and β thalassemia can be differentiated using the four indices. For example, three groups which include normal, iron deficiency anemia, and β thalassemia can be differentiated by performing multi group differentiation analysis of the four indices obtained from the measurement of the blood sample. That is, if one has, beforehand, the four indices information obtained by measuring a plurality of samples of normal blood, and blood of patients with iron deficiency anemia, and blood of patients with β thalassemia, then it is possible to determine to which group a blood sample belongs based on the indices obtained by measuring the blood sample. Easily understandable and useful information can be obtained by this differentiation analysis.

Although the functions and structure related to analysis and output performed by the blood cell analyzer of the present embodiment has been described in terms of being provided to the blood cell analyzer beforehand, the same functions may also be realized by a computer program, such that the functions of the present embodiment can be realized in a conventional blood cell analyzer by installing the computer program in the conventional blood cell analyzer.

Although a scattered light intensity histogram for mature red blood cells Rb generated from a scattergram obtained by measuring a RET sample is used as the RBC-Y histogram in the present embodiment, it is to be noted that a scattered light intensity histogram of reticulocytes Re and mature red blood cells Rb in the scattergram may also be used for the purpose.

Since the blood cell analyzer of the present invention calculates and analyzes a plurality of distribution data for target blood cells obtained by different particle detection principles as described above, information useful for the diagnosis and treatment of diseases can be obtained at low cost by comparing the distribution maps. Moreover, easily understandable information can be effectively obtained by outputting the distribution maps in the same format, and outputting the distribution maps together with the indices related to the distributions.

What is claimed is:

1. A blood cell analyzer comprising:
a first detection unit for electrically detecting blood cells in a blood sample;
a second detection unit for optically detecting blood cells in the blood sample;
a volume information obtainer for obtaining volume information of red blood cells based on the electrically detected blood cells by the first detection unit;
a scattered light intensity information obtainer for obtaining a scattered light intensity of red blood cells based on the optically detected blood cells by the second detection unit;
a first histogram preparer for preparing a first histogram of the volume information of the red blood cells obtained by the volume information obtainer;
a second histogram preparer for preparing a second histogram of the scattered light intensity information of the red blood cells obtained by the scattered light intensity information obtainer;
a display unit; and
a data processor for preparing a screen for displaying on the display unit, the screen including the first and second histograms prepared by the first and second histogram preparer that are displayed side by side for comparison, the data processor calculates first and second threshold values of volume displayed on the first histogram and calculates third and fourth threshold values of scattered light intensity displayed on the second histogram
wherein the data processor calculates a percentage of red blood cells which have volume information that is less than the first threshold value relative to all red blood cells (MicroR), a percentage of red blood cells which have volume information that is greater than the second threshold value relative to all red blood cells (MacroR), a percentage of red blood cells which have scattered light intensity information that is less than the third threshold value relative to all red blood cells (LScRBC), and a percentage of red blood cells which have scattered light intensity information that is greater than the fourth threshold value relative to all red blood cells (HScRBC).

2. The blood cell analyzer of claim 1, wherein the first histogram displays first and second demarcation lines corresponding to the first and the second threshold values, respectively, and the second histogram displays third and fourth demarcation lines corresponding to the third and the fourth threshold values.

3. The blood cell analyzer of claim 1, wherein the screen comprises a side-by side comparison of the first and second histograms, further wherein the calculated MicroR and the calculated LScRBC are compared between the first and second histograms.

4. The blood cell analyzer of claim 3, wherein a low value of MicroR and a high value for LScRBC indicates a presence of beta thalassemia.

5. The blood cell analyzer of claim 1, wherein the data processor prepares the screen including the first and second histograms side by side and displays a display region that includes a display of the calculated MicroR, the calculated MacroR, the calculated LScRBC and the calculated HScRBC.

6. The blood cell analyzer of claim 1, further comprising a measurement sample preparation unit for preparing a first measurement sample from predetermined amounts of blood sample and diluent, and preparing a second measurement sample from predetermined amounts of blood sample and diluent, and a stain for staining reticulocytes, wherein the first detection unit detects blood cells in the first measurement sample, and the second detection unit detects blood cells in the second measurement sample.

7. The blood cell analyzer of claim 6, wherein the data processor classifies red blood cells and reticulocytes and the scattered light intensity information obtainer obtains scattered light intensity information of each of classified red blood cell based on data obtained from each blood cell by the second detection unit.

* * * * *